United States Patent
Jessen

(10) Patent No.: US 6,784,158 B1
(45) Date of Patent: Aug. 31, 2004

(54) METHOD FOR PREPARING A COMPOUND WITH GROWTH HORMONE RELEASING PROPERTIES

(75) Inventor: Claus Ulrich Jessen, Vanløse (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/325,677

(22) Filed: Jun. 3, 1999

Related U.S. Application Data

(60) Provisional application No. 60/089,655, filed on Jun. 17, 1998.

(30) Foreign Application Priority Data

Jun. 9, 1998 (DK) ........................................ 1998 00776

(51) Int. Cl.[7] .............................................. C07K 5/06
(52) U.S. Cl. ........................ 514/19; 530/333; 562/553
(58) Field of Search ........................ 514/19; 530/333; 562/553

(56) References Cited

U.S. PATENT DOCUMENTS

| | | | |
|---|---|---|---|
| 3,673,208 A | * 6/1972 | Papaioannou | ............... 260/309 |
| 4,234,491 A | * 11/1980 | Cooper | .................... 260/340.9 |
| 4,351,762 A | * 9/1982 | Verlander | ................ 260/112.5 |

FOREIGN PATENT DOCUMENTS

| WO | 97/23508 | * 7/1997 |
|---|---|---|
| WO | WO 97/46252 | 12/1997 |

OTHER PUBLICATIONS

John H. Jones, "The Formation of Peptide Bonds: A General Survey", The Peptides, vol. 1, pp. 65–66, 1979.

* cited by examiner

*Primary Examiner*—Christopher S. F. Low
*Assistant Examiner*—David Lukton
(74) *Attorney, Agent, or Firm*—Reza Green; Rosemarie R. Wilk-Orescan; Richard W. Bork

(57) ABSTRACT

A method for preparing a compound of formula I

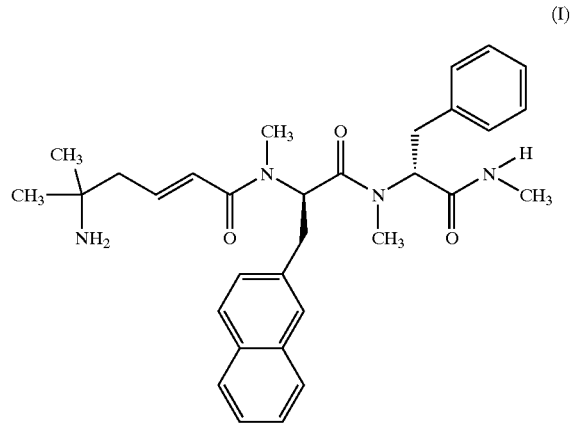

(I)

or a salt thereof is disclosed.

16 Claims, No Drawings

METHOD FOR PREPARING A COMPOUND WITH GROWTH HORMONE RELEASING PROPERTIES

CROSS-REFERENCE TO RELATED APPLICATIONS

This application claims priority under 35 U.S.C. 119 of Danish application 1998 00776 filed Jun. 9, 1998, and U.S. provisional application No. 60/089,655 filed on Jun. 17, 1998, the contents of which are fully incorporated herein by reference.

FIELD OF INVENTION

The present invention relates to a process for preparing a compound of formula I, a GH secretagogue which can be used i.a. in treating medical disorders resulting from a deficiency in growth hormone.

BACKGROUND OF THE INVENTION

Growth hormone is a hormone which stimulates growth of all tissues capable of growing. In addition, growth hormone is known to have a number of effects on metabolic processes, e.g., stimulation of protein synthesis and free fatty acid mobilisation and to cause a switch in energy metabolism from carbohydrate to fatty acid metabolism. Deficiency in growth hormone can result in a number of severe medical disorders, e.g., dwarfism.

Growth hormone is released from the pituitary. The release is under tight control of a number of hormones and neurotransmitters either directly or indirectly. Growth hormone release can be stimulated by growth hormone releasing hormone (GHRH) and inhibited by somatostatin. In both cases the hormones are released from the hypothalamus but their action is mediated primarily via specific receptors located in the pituitary. Other compounds which stimulate the release of growth hormone from the pituitary have also been described. For example arginine, L-3,4-dihydroxyphenylalanine (L-Dopa), glucagon, vasopressin, PACAP (pituitary adenylyl cyclase activating peptide), muscarinic receptor agonists and a synthetic hexapeptide, GHRP (growth hormone releasing peptide) release endogenous growth hormone either by a direct effect on the pituitary or by affecting the release of GHRH and/or somatostatin from the hypothalamus.

In disorders or conditions where increased levels of growth hormone is desired, the protein nature of growth hormone makes anything but parenteral administration non-viable. Furthermore, other directly acting natural secretagogues, e.g., GHRH and PACAP, are longer polypeptides for which reason parenteral administration is preferred. WO 97/23508 discloses a method for preparing the compound of formula I. This method is very expensive and makes use of reagents which are adverse to the environment.

It is an object of the present invention to provide a novel method for preparing a compound of formula I which method results in high yields and high purity. Moreover the present method is reproducible and more economic, and is suitable for large scale production.

SUMMARY OF THE INVENTION

In accordance with the present invention there is provided a novel and improved method for preparing a compound of formula I

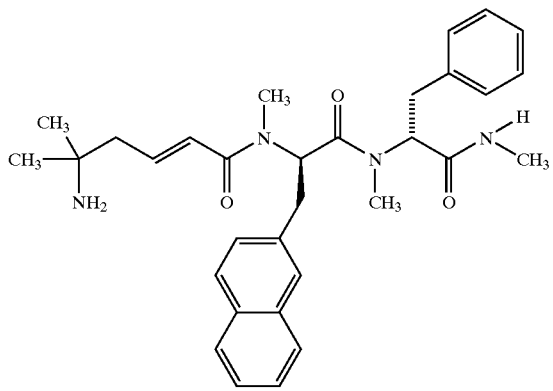

or a salt thereof, comprising a) treating a compound of formula II

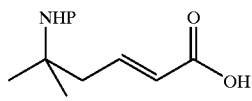

or a salt thereof, wherein P is a protecting group, with an agent capable of forming an amide or ester or mixed carbonic anhydride or anhydride or acid halide, in a solvent selected from an organic solvent or mixture of organic solvents or a mixture of organic solvent(s) and water, thereby producing and isolating a compound of formula III

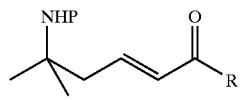

or a salt thereof, wherein R together with the carbonyl moiety is an amide or ester or mixed carbonic anhydride or anhydride or acid halide, b) treating the isolated compound of formula III, or a salt thereof, with a compound of formula (IV)

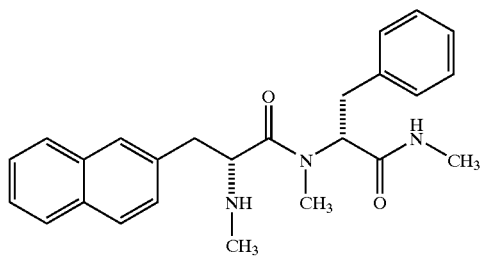

or a salt thereof, in a solvent selected from an organic solvent or mixture of organic solvents or a mixture of organic solvent(s) and water, thereby producing a compound of formula (V)

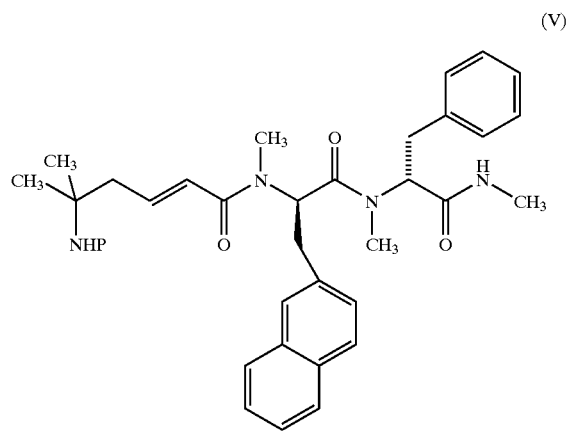

or a salt thereof, which is then deprotected in a conventional manner, to obtain the compound of formula (I) or a salt thereof.

DESCRIPTION OF THE INVENTION

Accordingly, the present invention relates to a method for preparing a compound of formula I

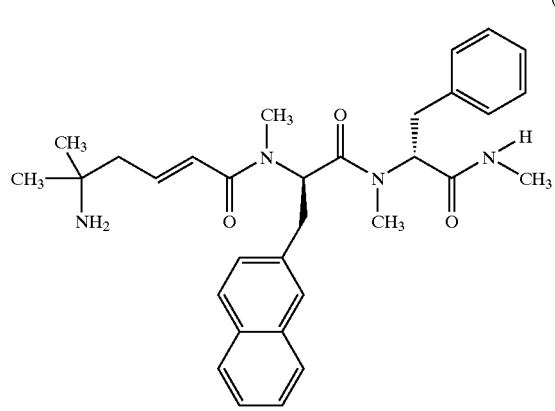

or a salt thereof, comprising a) treating a compound of formula II

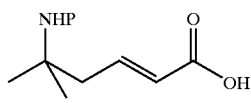

or a salt thereof, wherein P is a protecting group, with an agent capable of forming an amide or ester or mixed carbonic anhydride or anhydride or acid halide, in a solvent selected from an organic solvent or mixture of organic solvents or a mixture of organic solvent(s) and water, thereby producing and isolating a compound of formula III

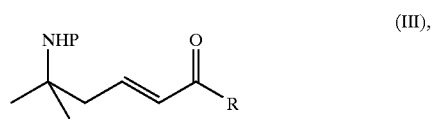

or a salt thereof, wherein R together with the carbonyl moiety is an amide or ester or mixed carbonic anhydride or anhydride or acid halide, b) treating the isolated compound of formula III, or a salt thereof, with a compound of formula (IV)

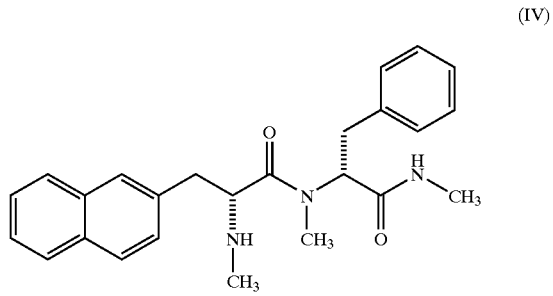

or a salt thereof, in a solvent selected from an organic solvent or mixture of organic solvents or a mixture of organic solvent(s) and water, thereby producing a compound of formula (V)

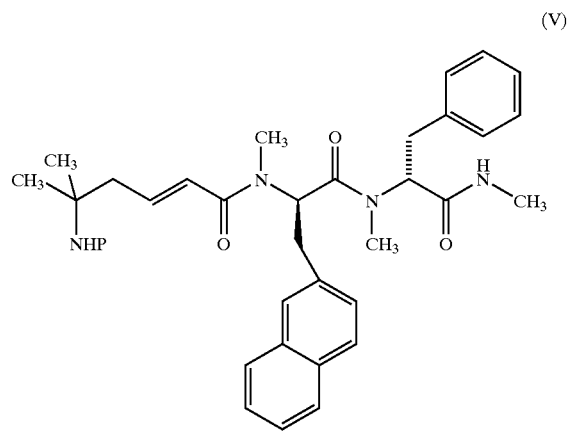

or a salt thereof, which is then deprotected in a conventional manner, to obtain the compound of formula (I) or a salt thereof.

In one embodiment of the present method P is a group of formula —C(=O)—$C_{1-12}$alkyl, —C(=O)—O—$C_{1-12}$alkyl, —C(=O)—$C_{1-12}$alkenyl or —C(=O)—O—$C_{1-12}$alkenyl, optionally substituted with one or more halogen, $C_{1-6}$alkyl, hetaryl, aryl or fused-ring aromatic system. P is preferably selected from —C(=O)H, Troc, Boc, and Fmoc. In one embodiment P is Troc. In a second embodiment P is Boc. In a third embodiment P is Fmoc. In a most preferred embodiment P is Troc.

In another embodiment of the present method the agent capable of forming an amide or ester or mixed carbonic anhydride or anhydride or acid halide is selected from benzotriazole, isobutyl chlorocarbonate, DHOBt, HOBt, HOSu, and HOAt. In a most preferred embodiment the agent capable of forming an amide or ester or mixed carbonic anhydride or anhydride or acid halide is DHOBt.

Furthermore the solvent in step b of the present method is preferably a mixture of an organic solvent and water, preferably an ester and water, such as $C_{1-6}$alkyl-C(=O)—O—$C_{1-6}$alkyl, e.g. ethylacetate and water.

The de-protection is usually carried out by acidic, basic, oxidative or reductive cleavage, e.g. when the protection group is Troc then reductive cleavage is carried out with Zn and acetic acid.

In a preferred embodiment of the present method P is Troc and the agent capable of forming an amide or ester or mixed carbonic anhydride or anhydride or acid halide is DHOBt.

In another aspect the present invention relates to a compound of formula III

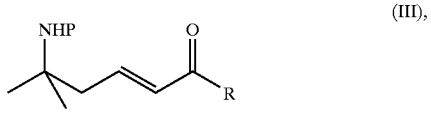

(III), or a salt thereof, wherein R together with the carbonyl moiety is an amide or ester or mixed carbonic anhydride or anhydride or acid halide, and P is a protecting group. In one embodiment P is a group of formula —C(=O)—$C_{1-12}$alkyl, —C(=O)—O—$C_{1-12}$alkyl, —C(=O)—$C_{1-12}$alkenyl or —C(=O)—O—$C_{1-12}$alkenyl, optionally substituted with one or more halogen, $C_{1-6}$alkyl, hetaryl, aryl or fused-ring aromatic system. P is preferably selected from —C(=O)H, Troc, Boc, and Fmoc. In one embodiment P is Troc. In a second embodiment P is Boc. In a third embodiment P is Fmoc. In a most preferred embodiment P is Troc. In a further embodiment the agent capable of forming an amide or ester or mixed carbonic anhydride or anhydride or acid halide is selected from benzotriazole, isobutyl chlorocarbonate, DHOBt, HOBt, HOSu, and HOAt, preferably DHOBt. In a most preferred embodiment P is Troc and said amide or ester or mixed carbonic anhydride or anhydride or acid halide is obtained by reacting DHOBt with the carboxylic acid moiety in the compound of formula II.

In a further aspect the present invention relates to a compound of formula V

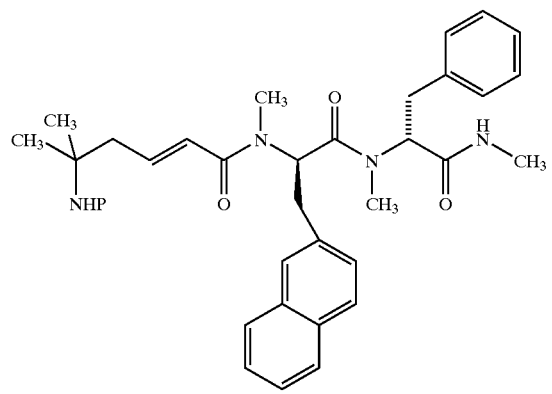

(V)

or a salt thereof, wherein P is Troc or Fmoc.

In one embodiment the compound is

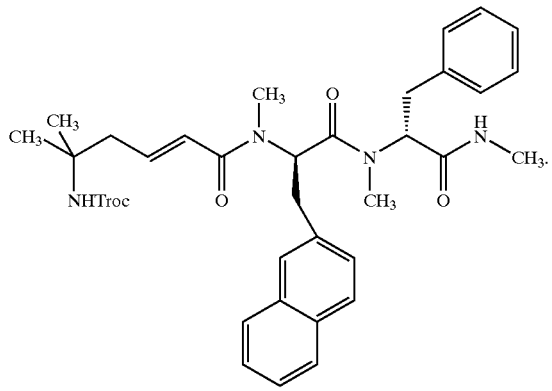

In a second embodiment the compound is

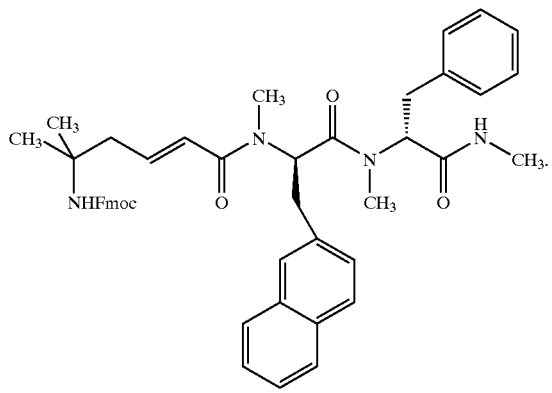

The compounds of the present invention, i.e. formula I, II, III, IV and V may optionally be on a salt form, such as a pharmaceutically acceptable salt form e.g. the pharmaceutically acceptable acid addition salts of compounds of formula I, II, III, IV and V, which include those prepared by reacting the compound of formula I, II, III, IV and V with an inorganic or organic acid such as hydrochloric, hydrobromic, sulfuric, acetic, phosphoric, lactic, malic, maleic, mandelic phthalic, citric, glutaric, gluconic, methanesulfonic, salicylic, succinic, tartaric, toluenesulfonic, trifluoracetic, sulfamic or fumaric acid and/or water.

Scheme 1

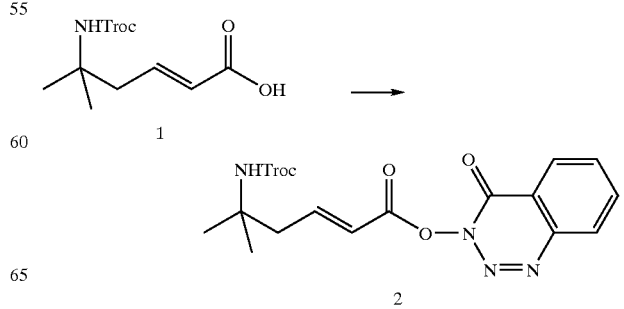

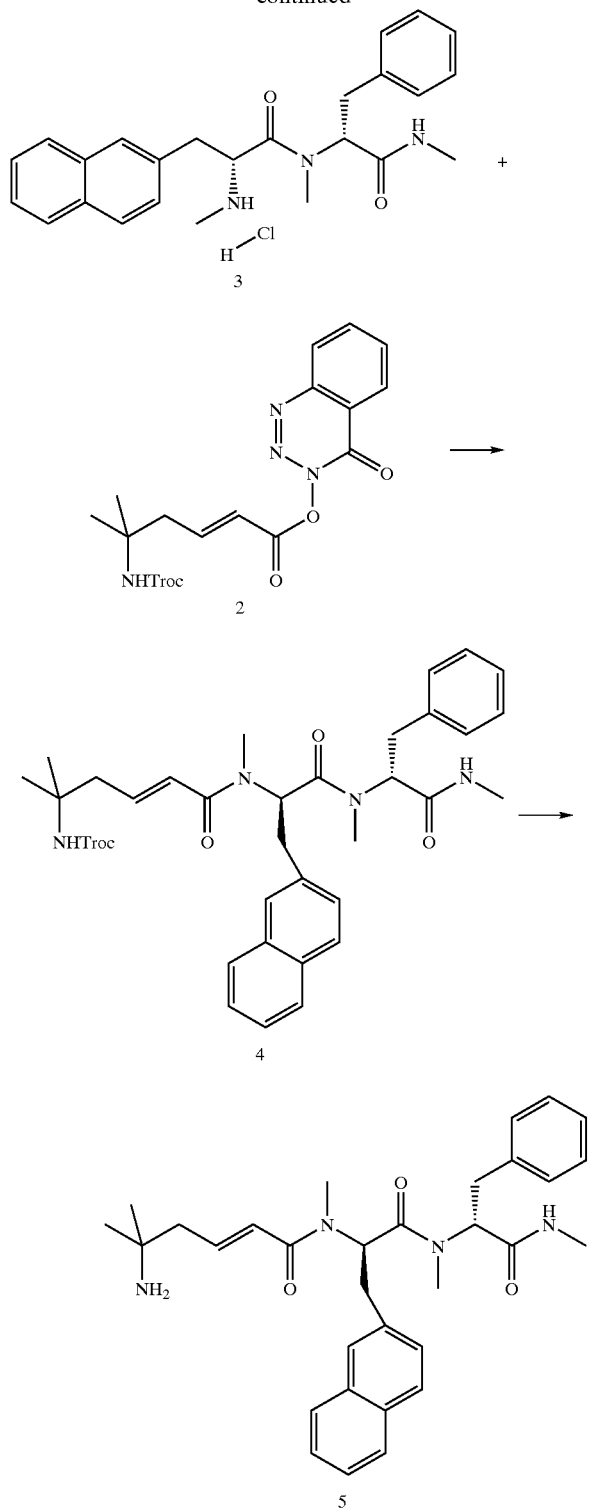

The process according to the present invention is illustrated in above scheme 1 and should in no way be interpreted as limiting the invention in any way. Thus, the above use of specific compounds are only for illustrative purposes.

The compound 1 is a commercially available compound or may be prepared from known starting materials by conventional reaction steps, for instance as illustrated in example 1, wherein 5-(N-Boc)-Amino-5-methyl-hex-(2E)-enoic acid disclosed in e.g. WO 97/23508 is converted to 5-(N-Troc)-Amino-5-methyl-hex-(2E)-enoic acid. It is possible to start from 5-(N-Boc)-Amino-5-methyl-hex-(2E)-enoic acid and introduce a suitable protecting group, such as a group of formula —C(=O)—$C_{1-12}$alkyl, —C(=O)—O—$C_{1-12}$alkyl, —C(=O)—$C_{1-12}$alkenyl or —C(=O)—O—$C_{1-12}$alkenyl, optionally substituted with one or more halogen, $C_{1-6}$alkyl, hetaryl, aryl or fused-ring aromatic system, e.g. a protecting group selected from —C(=O)H, trichloroethyloxycarbonyl (Troc), tert-butyloxycarbonyl (Boc), and fluorenylmethyloxycarbonyl (Fmoc), preferably Troc, using a similar procedure as described in example 1 herein. Compound 1 is then reacted with an agent capable of forming an amide or ester or mixed carbonic anhydride or anhydride or acid halide, such as benzotriazole, isobutyl chlorocarbonate, 3,4-Dihydro-3-hydroxy-4-oxo-1,2,3-benzotriazine (DHOBt), N-hydroxy benzotriazol (HOBt), N-hydroxy succinimid (HOSu), and 1-hydroxy-7-azabenzotriazole (HOAt), preferably DHOBt, in a solvent selected from an organic solvent or mixture of organic solvents or a mixture of organic solvent(s) and water, such as ethylacetate, thereby producing the compound 2, which is isolated in a conventional manner, e.g. as described in connection with example 2 herein. The isolated compound 2, which is very crystallinic and thus easy to handle, is treated with compound 3, either as the free amine or as a salt, e.g. the HCl salt, in a solvent selected from an organic solvent or mixture of organic solvents or a mixture of organic solvent(s) and water, preferably a mixture of an organic solvent and water, such as an ether and water, e.g. THF and water, preferably an ester and water, such as $C_{1-6}$alkyl-C(=O)—O—$C_{1-6}$alkyl, e.g. ethylacetate and water, thereby producing compound 4, which is then deprotected in a conventional manner, such as by reductive cleavage with an organic acid, such as acetic acid and Zn, or the like, to obtain the compound 5, which is the compound of formula 1. The compound 3 may be obtained as described in WO 97/23508.

In the above structural formulas and throughout the present specification, the following terms have the indicated meanings:

The $C_{1-12}$-alkyl, $C_{1-6}$-alkyl, or $C_{1-4}$-alkyl groups specified herein are intended to include those alkyl or alkylene groups of the designated length in either a linear or branched or cyclic configuration. Examples of linear alkyl are methyl, ethyl, propyl, butyl, pentyl, hexyl and heptyl. Examples of branched alkyl are isopropyl, sec-butyl, tert-butyl, isopentyl, isohexyl and isoheptyl. Examples of cyclic alkyl are $C_{3-12}$-cycloalkyl such as cyclopropyl, cyclobutyl, cyclopentyl, cyclohexyl and cycloheptyl. The $C_{1-6}$-alkoxy groups specified herein are intended to include an oxygen atom connected to a $C_{1-6}$-alkyl as defined above. Examples are methoxy, ethoxy, isopropyloxy, sec-butyloxy, tert-butyloxy, cyclopropyloxy, cyclobutyloxy, etc.

The term "aryl" is intended to include monovalent carbocyclic aromatic ring moieties, being either monocyclic, bicyclic or polycyclic, e.g. selected from the group consisting of phenyl and naphthyl, optionally substituted with one or more $C_{1-6}$-alkyl, $C_{1-6}$-alkoxy, halogen, amino or aryl. Such aryl groups are described in Morrison and Boyd "Organic Chemistry", 4. Ed.

The term "hetaryl" is intended to include monovalent heterocyclic aromatic ring moieties, being either monocyclic, bicyclic or polycyclic, e.g. selected from the group consisting of pyridyl, 1-H-tetrazol-5-yl, thiazolyl, imidazolyl, indolyl, pyrimidinyl, thiadiazolyl, pyrazolyl, oxazolyl, isoxazolyl, oxadiazolyl, thienyl, quinolinyl, pyrazinyl, or isothiazolyl, optionally substituted by one or more $C_{1-6}$alkyl, $C_{1-6}$-alkoxy, halogen, amino or aryl. Such hetaryl groups are described in Morrison and Boyd "Organic Chemistry", 4. Ed.

The term "fused-ring aromatic system" is intended to include monovalent aromatic ring moieties, being either bicyclic or polycyclic hydrocarbons, such as a system selected from the group consisting of fluorenes, e.g. flourenyl. Such fused-ring aromatic systems are described in Morrison and Boyd "Organic Chemistry", 4. Ed.

The term "halogen" is intended to include chlorine (Cl), fluorine (F), bromine (Br) and iodine (I).

The term "Protecting group" is intended to include any group which protect the amino group when the carboxylic group in the compound of formula II is subjected to functional derivatization, and which is easy to remove afterwards by cleavage. Such protecting groups are described in "Protective groups in organic chemistry", 2. Ed, Greene, T. W.; Wuts, P. G. M., John Wiley&Sons,Inc. 1991; and "The Peptides, Analysis, Synthesis, Biology", vol 3 "Protection of Functional Groups in Peptide synthesis", Gross, E.; Meienhofer, J.; Academic Press. A suitable protecting group is a group of formula —C(=O)—$C_{1-12}$alkyl, —C(=O)—O—$C_{1-12}$alkyl, —C(=O)—$C_{1-12}$alkenyl or —C(=O)—O—$C_{1-12}$alkenyl, optionally substituted with one or more halogen, $C_{1-6}$-alkyl, hetaryl, aryl or fused-ring aromatic system, e.g. Troc, Boc, and Fmoc.

The term "agent capable of forming an amide or ester or mixed carbonic anhydride or anhydride or acid halide" is intended to include such agents which activates the compound by forming a functional derivative which may be used in acylation. Such agents are described in "The Peptides, Analysis, Synthesis, Biology", vol 1 "Major Methods of Bond Formation", Gross, E.; Meienhofer, J.; Academic Press, 1981. Suitable agents are selected from benzotriazole, isobutyl chlorocarbonate, DHOBt, HOBt, HOSu, and HOAt.

The term "de-protection" is intended to include acidic, basic, oxidative or reductive cleavage as described in "The Peptides, Analysis, Synthesis, Biology", vol 1 "Major Methods of Bond Formation", Gross, E.; Meienhofer, J.; Academic Press, 1981. When, for instance, the protection group is Troc then reductive cleavage is carried out with Zn and acetic acid.

The compounds of formula I when used for the intended purpose of releasing endogenous growth hormone may be administered in pharmaceutically acceptable acid addition salt form or, where appropriate, as a alkali metal or alkaline earth metal or lower alkylammonium salt. Such salt forms are believed to exhibit approximately the same order of activity as the free base forms.

The compounds of the general formula I possess the ability to release endogenous growth hormone in vivo as mentioned in WO 97/23508. The compounds may therefore be used in the treatment of conditions which require increased plasma growth hormone levels such as in growth hormone deficient humans or in elderly patients or livestock.

To those skilled in the art, it is well known that the current and potential uses of growth hormone in humans are varied and multitudinous. Thus, compounds of formula I can be administered for purposes stimulating release of growth hormone from the pituitary and would then have similar effects or uses as growth hormone itself. Compounds of formula I are useful for stimulation of growth hormone release in the elderly, prevention of catabolic side effects of glucocorticoids, prevention and treatment of osteoporosis, treatment of chronic fatigue syndrom (CFS), treatment of acute fatigue syndrom and muscle loss following election surgery, stimulation of the immune system, acceleration of wound healing, accelerating bone fracture repair, accelerating complicated fractures, e.g. disctraction osteogenesis, treatment of wasting secondary to fractures, treatment of growth retardation, treating growth retardation resulting from renal failure or insufficiency, treatment of cardiomyopathy, treatment of wasting in connection with chronic liver disease, treatment of thrombocytopenia, treatment of growth retardation in connection with Crohn's disease, treatment of short bowel syndrome, treatment of wasting in connection with chronic obstructive pulmonary disease (COPD), treatment of complications associated with transplantation, treatment of physiological short stature including growth hormone deficient children and short stature associated with chronic illness, treatment of obesity and growth retardation associated with obesity, treatment of anorexia, treatment of growth retardation associated with the Prader-Willi syndrome and Tumer's syndrome; increasing the growth rate of a patient having partial growth hormone insensitive syndrome, accelerating the recovery and reducing hospitalization of burn patients; treatment of intrauterine growth retardation, skeletal dysplasia, hypercortisolism and Cushing's syndrome; induction of pulsatile growth hormone release; replacement of growth hormone in stressed patients, treatment of osteochondrodysplasias, Noonan's syndrome, schizophrenia, depressions, Alzheimer's disease, delayed wound healing and psychosocial deprivation, treatment of catabolism in connection with pulmonary dysfunction and ventilator dependency, treatment of cardiac failure or related vascular dysfunction, treatment of impaired cardiac function, treatment or prevention of myocardial infarction, lowering blood pressure, protection against ventricular dysfunction or prevention of reperfusion events, treatment of adults in chronic dialysis, attenuation of protein catabolic responses after major surgery, reducing cachexia and protein loss due to chronic illness such as cancer or AIDS; treatment of hyperinsulinemia including nesidioblastosis, adjuvant treatment for ovulation induction; stimulation of thymic development and prevention of the age-related decline of thymic function, treatment of immunosuppressed patients, treatment or sarcopenia, treatment of wasting in connection with AIDS, improvement in muscle strength, mobility, maintenance of skin thickness, treatment of metabolic homeostasis and renal homeostasis in the frail elderly, stimulation of osteoblasts, bone remodelling and cartilage growth, regulation of food intake, stimulation of the immune system in companion animals and treatment of disorders of aging in companion animals, promoting growth in livestock and stimulation of wool growth in sheep, increasing milk production in livestock, treatment of metabolic syndrome (syndrome X), treatment of insulin resistance, including NIDDM, in mammals, e.g. humans, treatment of insulin resistance in the heart, improvement of sleep quality and correction of the relative hyposomatotropism of senescence due to high increase in REM sleep and a decrease in REM latency, treatment of hypothermia, treatment of frailty associated with aging, treatment of congestive heart failure, treatment of hip fractures, treatment of immune deficiency in individuals with a depressed T4/T8 cell ratio, treatment of muscular atrophy, treatment of musculoskeletal impairment in elderly, enhancing the activity of protein kinase B (PKB), improvement of the overall pulmonary function, and treatment of sleep disorders. Treatment is also intended to include prophylactic treatment.

For the above indications the dosage will vary depending on the compound of formula I employed, on the mode of administration and on the therapy desired. The dosage of the compounds according to this invention is suitably 0.01–500 mg/day, e.g. from about 5 to about 50 mg, such as about 10 mg per dose, when administered to patients, e.g. humans, as a drug. However, generally dosage levels between 0.0001 and 100 mg/kg body weight daily are administered to patients and animals to obtain effective release of endogenous growth hormone. Morever the compounds of formula I have no or substantially no side-effects, when administered in the above dosage levels, such side-effects being e.g. release of LH, FSH, TSH, ACTH, vasopressin, oxytocin, cortisol and/or prolactin. Usually, dosage forms suitable for oral, nasal, pulmonal or transdermal administration comprise from about 0.0001 mg to about 100 mg, preferably from about 0.001 mg to about 50 mg of the compounds of formula I admixed with a pharmaceutically acceptable carrier or diluent.

Optionally, a pharmaceutical composition comprising the compound of formula I prepared by the method of the invention may be combined with one or more compounds exhibiting a different activity, e.g., an antibiotic or other pharmacologically active material.

The route of administration may be any route which effectively transports the active compound to the appropriate or desired site of action, such as oral, nasal, pulmonary, transdermal or parenteral, the oral route being preferred.

Apart from the pharmaceutical use of the compounds of formula I, they may be useful in vitro tools for investigating the regulation of growth hormone release.

Compounds of formula I may also be useful in vivo tools for evaluating the growth hormone releasing capability of the pituitary. For example, serum samples taken before and after administration of these compounds to humans can be assayed for growth hormone. Comparison of the growth hormone in each serum sample would directly determine the ability of the patients pituitary to release growth hormone.

Compounds of formula I may be administered to commercially important animals to increase their rate and extent of growth, and to increase milk production.

A further use of growth hormone secretagogue compounds of formula I is in combination with other secretagogues such as GHRP (2 or 6), GHRH and its analogues, growth hormone and its analogues or somatomedins including IGF-1 and IGF-2.

EXAMPLES

The process for preparing compounds of formula I is further illustrated in the following examples, which however, are not to be construed as limiting.

The structures of the compounds are confirmed by either elemental analysis (MA) nuclear magnetic resonance (NMR) or mass spectrometry (MS). NMR shifts (d) are given in parts per million (ppm) and only selected peaks are given. mp is melting point and is given in °C. Column chromatography was carried out using the technique described by W. C. Still et al, J. Org. Chem. 1978, 43, 2923–2925 on silica gel 60. Compounds used as starting materials are either known compounds or compounds which can readily be prepared by methods known per se.

Example 1

Synthesis of 5-(N-Troc)-amino-5-methyl-hex-2E-enoic Acid 104 g (0.43 mol) 5-(N-Boc)-Amino-5-methyl-hex-(2E)-enoic acid is dissolved in 800ml of ethylacetate (EtOAc). The mixture is cooled to 0–5° C. on an ice bath and HCl gas is bubbled to the mixture while stirring. Precipitation occurs after 20 min. The temperature rises to max15° C. via control of HCl addition. App. 92 g of HCl gas is used to complete the reaction. The reaction is followed via HPLC. The next day the mixture is evaporated to halve volume and stripped with 2×100 ml EtOAc in order to remove HCl. The mixture is kept at 0–5° C. for 4 h. The resulting precipitate is isolated and dried at 30° C. in the vacuum to constant yield. The yield of 5-Amino-5-methyl-hex-(2E)-enoic acid, HCl is 73 g (95%). The HCl salt is dissolved in 730 ml $NaHCO_3$/NaOH buffer, pH 11, and 730 ml 2-PrOH, pH is approx. 9.5. Cooled to0–5° C. Succinimidyl-2,2,2-trichloroethylcarbonate (TrocOSu) is added in 3 portions over 1.5 hours. pH is maintained at 9.5–10 with 2M NaOH (approx. 75 ml). Precipitation occurs. The mixture is stirred overnight at 0–5° C. to complete the reaction. The reaction mixture (pH 9.1) is filtered. The 2-propanol (2-PrOH) content in the filtrate is distilled off under vacuum (30° C.). pH is adjusted to 9.5 with 2M NaOH. 500 ml methyl-tert-butylether (MTBE) are added. 3 phases occur. The two lower phases which contains the product are isolated. The organic MTBE phase is extracted with 300 ml water (pH 10, adjusted with aq. NaOH).

The aqueous phases are combined and 500 ml of MTBE are added. The mixture is acidified to pH 2 with 4M HCl at ambient temperature. Evolution of $CO_2$ gas. The organic phase is isolated and the water phase extracted with 500 ml MTBE. The combined organic phases are dried. Evaporation of solvent yields 131 g of 5-(N-Troc)-amino-5-methyl-hex-(2E)-enoic acid (100%). It is isolated as an oil which slowly crystallises.

Example 2

5-(N-Trichloroethyl-oxycarbonyl)-amino-5-methyl-hex-(2E)-en-(3,4-Dihydro-3-hydroxy4-oxo-1,2,3-benzotriazine) acid Ester 102 g of 5-(N-Trichloroethyloxycarbonyl)-amino-5-methyl-hex-(2E)-enoic acid and 66 g of 3,4-Dihydro-3-hydroxy4-oxo-1,2,3-benzotriazine (DHOBt) are added to 1000 ml EtOAc while stirring. The mixture is cooled to 0 to −5° C. and 52 g dicyclohexyl carbodiimide (DCC) dissolved in 300 ml EtOAc is added over 1 hour under nitrogen atmosphere. The solution is stirred overnight at 0 to −5° C. to complete the reaction. The solution is warmed up to ambient temperature and filtered. The EtOAc content in the filtrate is distilled off under vacuum (30° C.) and replaced with 2-PrOH. Residual EtOAc is stripped off with 2-PrOH (2×200 ml). The raw product is re-crystallised in 950 ml of 2-PrOH. Crystallisation starts at 70° C. The mixture is slowly cooled to 0–5° C. and stirred overnight at 0–5° C. The mixture is filtered and washed with 2-PrOH. The filter cake is dried under vacuum to constant weight. The yield is 93 g of 5-(N-Trichloroethyl-oxycarbonyl)-amino-5-methyl-hex-2E-en-(3,4-Dihydro-3-hydroxy-4-oxo-1,2,3-benzotriazine) acid ester (63%). White crystals.

Example 3

Synthesis of 5-(N-Trichloroethyloxycarbonyl) amino-5-methylhex-(2E)-enoic acid N-methyl-N-((1R)-1-(N-methyl-N-((1R)-1-(methylcarbamoyl)-2-phenylethyl)carbamoyl)-2-(2-naphthyl)ethyl)amide A 2 L reactor is equipped with a mechanical stirrer, thermometer, heating facility and $N_2$-inlet. 80.2 g N-Methyl-N-((1R)-1-(N-methyl-N-((1R)-1-(methylcarbamoyl)-2-phenylethyl)carbamoyl)-2-(2-naphthyl)ethyl)amide, HCl is suspended in 540 ml EtOAc at 20–25° C. 18.6 g N-methyl morpholine (NMM) and thereafter 540 ml water is added. N-Methyl-N-((1R)-1-(N-methyl-N-((1R)-1-(methylcarbamoyl)-2-phenylethyl)carbamoyl)-2-(2-naphthyl)ethyl)amide, HCl slowly dissolves. After most of N-Methyl-N-((1R)-1-(N-methyl-N-((1R)-1-(methylcarbamoyl)-2-phenylethyl)carbamoyl)-2-(2-naphthyl)ethyl)amide, HCl is dissolved 5-(N-Trichloroethyl-oxycarbonyl)-amino--5-methyl-hex-2E-en-(3,4-Dihydro-3-hydroxy4-oxo-1,2,3-benzotriazine) acid ester is put into the reactor and the mixture is heated to 50–55° C. The temperature is retained at 50–55° C. for 24–48 h in order to complete the reaction. After cooling 200 ml EtOAc is added and the organic layer isolated. The organic layer is washed with 1×500 ml 0.5M KHSO$_4$, 1×500 ml sat.NaHCO$_3$ and 1×300 ml water. Thereafter the organic phase is dried over MgSO$_4$ and filtered leaving 146 g of title compound (>100%, contains EtOAc) oil/foam after evaporation.

The utilisation of 37.2 g instead of 18.6 g NMM enhances significantly the reactivity and the reaction is finished in less than 24 hours.

Example 4

Synthesis of Compound of Formula I

A 1 L reactor is equipped with a mechanical stirrer, thermometer, heating/cooling facility, dropping funnel and N$_2$-inlet. 35.3 g activated Zn dust (<60 μm) is suspended in 162 ml acetic acid. 5-(N-Trichloroethyloxycarbonyl)amino-5-methylhex-(2E)-enoic acid N-methyl-N-((1R)-1-(N-methyl-N-((1R)-1-(methylcarbamoyl)-2-phenylethyl) carbamoyl)-2-(2-naphthyl)ethyl)amide dissolved in 162 ml EtOAc is slowly added over 3 h. Heat and gas is developed, especially in the beginning. The temperature is kept at 30–35° C. for 18–24 h in order to complete the reaction. Next day the mixture is cooled to 20–25° C. and 200 ml EtOAc and 600 ml water are added. H$_2$ is developed. The reaction mixture is filtered and the water phase isolated. The organic layer is extracted with 1×500 ml and 1×100 ml 0.1M HCl. 800 ml EtOAc is added to the combined water phases and the pH is adjusted to 9 with 400 ml 25% NH$_3$ in water. The temperature is kept at 15–25° C. The organic layer is isolated and the water phase extracted with 400 ml EtOAc. The combined organic phase is washed with 1×500 ml and 1×250 ml 1% NH$_3$ in water, dried over MgSO$_4$, filtered and evaporated to dryness leaving 94 g of the compound of formula I (99%, contains EtOAc). Off white foam/oil.

Example 5

Synthesis of Compound of Formula I using Fmoc as Protection Group

The synthesis of the compound of formula I could be performed using the same methods as described in examples 1–4 but with Fmoc as proctection group instead of Troc.

In that case the steps would be synthesis of 5-(N-Fmoc)-amino-5-methyl-hex-2E-enoic acid, followed by synthesis of 5-(N-Fluorenylmethyloxycarbonyl)-amino-5-methyl-hex-(2E)-en-(3,4-Dihydro-3-hydroxy4-oxo-1,2,3-benzotriazine) acid ester, followed by synthesis of 5-(N-Fluorenylmethyloxycarbonyl)amino-5-methylhex-(2E)-enoic acid N-methyl-N-((1R)-1-(N-methyl-N-((1R)-1-(methylcarbamoyl)-2-phenylethyl)carbamoyl)-2-(2-naphthyl)ethyl)amide using 18.6 g of NMM and keeping pH below 7. This compound is deprotected to the compound of formula I.

Reference Example

Preparation of the Compound of Formula I as Described in WO97/23508

3-Hydroxy-1,1-dimethylpropylcarbamic acid tert-butyl ester

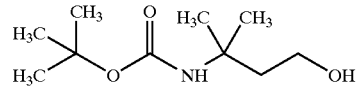

Step A

At 0° C., ethyl chloroformate (1.10 mL, 11.5 mmol) was given dropwise to a solution of 3-tert-butoxycarbonylamino-3-methylbutanoic acid (2.50 g, 11.5 mmol) and triethylamine (1.92 mL, 13.8 mmol) in tetrahydrofuran (10 mL). The solution was stirred for 40 min at 0° C. The formed precipitate was filtered off and washed with tetrahydrofuran (20 mL). The liquid was immediately cooled to 0° C. A 2M solution of lithium boronhydride in tetrahydrofuran (14.4 mL, 28.8 mmol) was added dropwise. The solution was stirred at 0° C. for 2 h, and then warmed to room temperature over a period of 4 h. It was cooled to 0° C. Methanol (5 mL) was added carefully. 1N Hydrochloric acid (100 mL) was added. The solution was extracted with ethyl acetate (2×100 mL, 3×50 mL). The combined organic layers were washed with saturated sodium hydrogen carbonate solution (100 mL) and dried over magnesium sulfate. The solvent was removed in vacuo. The crude product was chromatographed on silica (110 g) with ethyl acetate/heptane 1:2 to give 1.84 g of 3-hydroxy-1,1-dimethylpropylcarbamic acid tert-butyl ester.

3-(tert-Butoxycarbonylamino)-3-methylbutanal

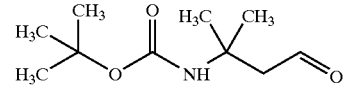

Step B

DMSO (1.22 mL, 17.2 mmol) was added to a solution of oxalyl chloride (1.1 mL, 12.9 mmol) at −78° C. in dichloromethane (15 mL). The mixture was stirred for 15 min at −78° C. A solution of 3-hydroxy-1,1-dimethylpropylcarbamic acid tert-butyl ester (1.75 g, 8.6 mmol) in dichloromethane (10 mL) was added dropwise over a period of 15 min. The solution was stirred at −78° C. for another 15 min. Triethylamine (6.0 mL, 43 mmol) was added. The solution was stirred at −78° C. for 5 min and then warmed to room temperature. The solution was diluted with dichloromethane (100 mL) and extracted with 1N hydrochloric acid (100 mL). The aqueous phase was extracted with dichloromethane (50 mL). The combined organic layers were washed with saturated sodium hydrogen carbonate solution (100 mL) and dried over magnesium sulfate. The solvent was removed in vacuo. The crude product was purified by column chromatography on silica (140 g) with ethyl acetate/heptane (1:3) to give 1.10 g of 3-(tert-butoxycarbonylamino)-3-methylbutanal.

Ethyl (2E)-5-(tert-Butoxycarbonylamino)-5-methylhex-2-enoate

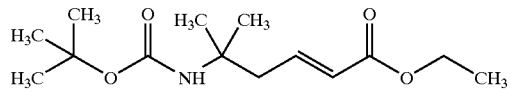

Step C

Triethylphoshonoacetate (1.96 mL, 9.8 mmol) was dissolved in tetrahydrofuran (30 mL). Potassium tert-butoxide (1.10 g, 9.8 mmol) was added. The solution was stirred for 40 min at room temperature. A solution of 3-(tert-butoxycarbonylamino)-3-methylbutanal (1.10 g, 5.5 mmol) in Tetrahydrofuran (6 mL) was added. The solution was stirred at room temperature. for 75 min. It was diluted with ethyl acetate (100 mL) and 1 N hydrochloric acid (100 mL). The phases were separated. The aqueous phase was extracted with ethyl acetate (2×50 mL). The combined organic phases were washed with saturated sodium hydrogen carbonate solution (60 mL) and dried over magnesium sulfate. The solvent was removed in vacuo. The crude product was purified by column chromatography on silica (90 g) with ethyl acetate/hepatane (1:4) to give 1.27 g of ethyl (2E)-5-(tert-butoxycarbonylamino)-5-methylhex-2-enoate.

(2E)-5-(tert-Butoxycarbonylamino)-5-methylhex-2-enoic Acid

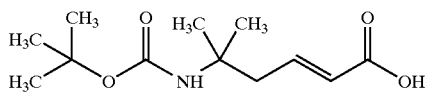

Step D

Ethyl (2E)-5-(tert-butoxycarbonylamino)-5-methylhex-2-enoate (1.233 g, 4.54 mmol) was dissolved in dioxane (20 mL). Lithium hydroxide (0.120 g, 5.00 mmol) was added as a solid. Water (10 mL) was added, until a clear solution was reached. The solution was stirred 16 h at room temperature. The solution was diluted with water (70 mL) and was extracted with tert-butyl methyl ether (2×100 mL). The aqueous phase was acidified with 1 N sodium hydrogensulfate solution (pH=1) and was extracted with tert-butylmethylether (3×70 mL). The organic phases were combined and dried over magnesium sulfate. The solvent was removed in vacuo to give 1.05 g of (2E)-5-(tert-butoxycarbonylamino)-5-methylhex-2-enoic acid. The crude product was used for further syntheses.

N-Methyl-N-((R)-1-(methylcarbamoyl)-2-phenylethyl)carbamic acid tert-butyl Ester

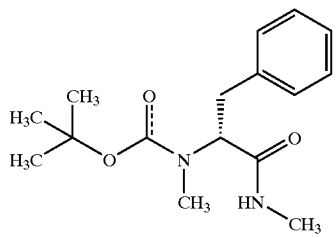

Step E

N-Tert-butoxycarbonyl-N-methyl-D-phenylalanine (1.22 g, 4.4 mmol), 1-hydroxybenzotriazole hydrate(0.59 g, 4.4 mmol) and 1-ethyl-3-(3-dimethylaminopropyl)carbodiimid hydrochloride (0.88 g, 4.6 mmol) were dissolved in N,N-dimethylformamide (25 mL) and stirred for 30 min. Methylamine (0.51 g of a 40% solution in methanol, 6.6 mmol) was added and the mixture was stirred overnight. Methylene chloride (80 mL) and water (100 mL) were added and the phases were separated. The organic phase was washed with sodium hydroxide (20 mL, 1N), sodium hydrogensulfate (50 mL, 10 %) and water (50 mL). The organic phase was dried (magnesium sulfate) and the solvent removed in vacuo to afford 1.39 g of N-methyl-N-((R)1-(methylcarbamoyl)-2-phenylethyl)carbamic acid tert-butyl ester.

(R)-N-Methyl-2-methylamino-3-phenylpropionamide

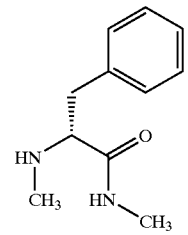

Step F

N-Methyl-N-((R)1-(methylcarbamoyl)-2-phenylethyl) carbamic acid tert-butyl ester (1.39 g, 7.23 mmol) was dissolved in a mixture of trifluoroacetic acid (5 mL) and methylene chloride (10 mL) and stirred for 45 min. The volatiles were removed in vacuo and the residue was stirred with a mixture of ethyl acetate (100 mL) and water (100 mL). Sodium hydrogen carbonate (50 mL, saturated) was added and the phases were separated. The organic phase was dried (magnesium sulfate) and the solvent removed in vacuo to afford 330 mg of (R)-N-methyl-2-methylamino-3-phenylpropionamide.

N-Methyl-N{(1R)-1-(N-methyl-N-((1R)-1-(methylcarbamoyl)-2-phenylethyl)carbamoyl)-2-(2-naphthyl)ethyl}carbamic acid tert-butyl Ester

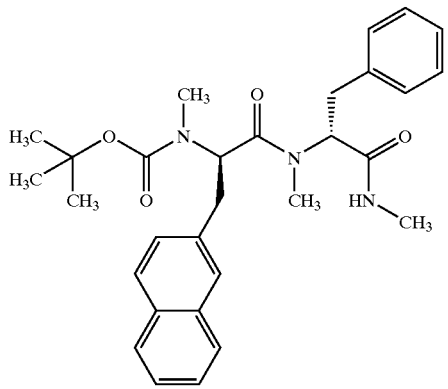

Step G (R)-Tert-butoxycarbonyl-N-methylamino-3-(2-naphthyl) propionic acid (548 mg, 1.66 mmol) was dissolved in methylene chloride (5 mL); 1-hydroxy-7-azabenzotriazole (227 mg, 1.66 mmol) was added along with N,N-dimethylformamide (2 mL). 1-Ethyl-3-(3-dimethylaminopropyl)carbodiimide hydrochloride (351 mg, 1.83 mmol) was added and the solution was stirred for 15 min. (R)-N-Methyl-2-methylamino-3-phenylpropionamide (320 mg, 1.66 mmol) dissolved in methylene chloride (4 mL) and diisopropylethylamine (0.28 mL, 1.66 mmol) were added and the mixture was stirred overnight. Methylene chloride (50 mL) was added and the organic phase was washed with water (100 mL), sodium hydrogensulfate (50 mL, 5%) and sodium hydrogen carbonate (50 mL, saturated). The organic phase was dried (magnesium sulfate) and the solvent removed in vacuo. The residue was chromatographed (silica, 2×45 cm) using ethylacetate/methylene chloride (1:1) to afford 604 mg of N-methyl-N-{(1R)-1-(N-methyl-N-((1R)-1-(methylcarbamoyl)-2-phenylethyl) carbamoyl)-2-(2-naphthyl)-ethyl}carbamic acid tert-butyl ester.

(2R)-N-Methyl-2-methylamino-N-((1R)-1-(methylcarbamoyl)-2-phenylethyl)-3-(2-naphthyl)propionamide

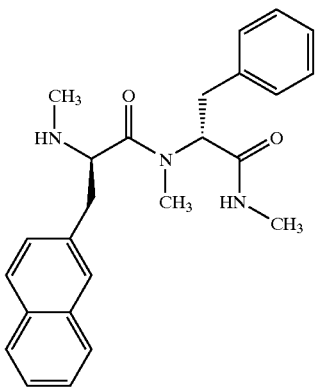

Step H

N-Methyl-N-{(1R)-1-(N-methyl-N-((1R)-1-(methylcarbamoyl)-2-phenylethyl)carbamoyl)-2-(2-naphthyl)ethyl}carbamic acid tert-butyl ester (600 mg, 1.19 mmol) was stirred in trifluoroacetic acid/methylene chloride (1:1, 5 mL) for 10 min and the volatiles were removed in vacuo. The residue was stripped with diethylether (2×5 mL) and dissolved in methanol (2 mL) and mixed with sodium hydrogen carbonate (10 mL) and ethylacetate (15 mL). The organic phase was separated and dried (magnesium sulfate) to afford 420 mg of (2R)-N-methyl-2-methylamino-N-((1R)-1-(methylcarbamoyl)-2-phenylethyl)-3-(2-naphthyl)propionamide.

((3E)-1,1-Dimethyl4-(N-methyl-N-((1R)-1-(N-methyl-N-((1R)-1-(methylcarbamoyl)-2-phenylethyl)carbamoyl)-2-(2-naphthyl)ethyl)carbamoyl)but-3-enyl)carbamic acid tert-butyl Ester

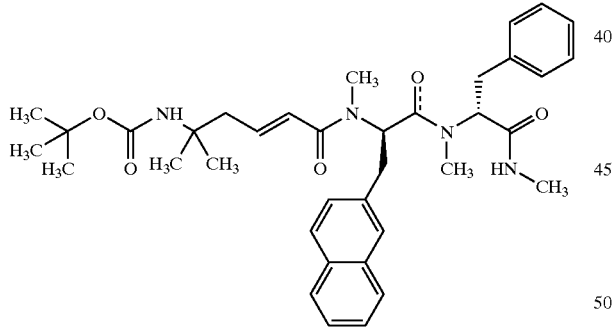

Step I (2E)-5-(tert-Butyloxycarbonylamino)-5-methylhex-2-enoic acid (200 mg, 0.82 mmol), 1-hydroxy-7-azabenzotriazole (112 mg, 0.82 mmol) and 1-ethyl-3-(3-dimethylaminopropyl)-carbodiimide hydrochloride (173 mg, 0.90 mmol) were dissolved in a mixture of methylene chloride (10 mL) and N,N-dimethylformamide (1 mL) and stirred for 15 min. N-Methyl-2-methylamino-N-((1R)-1-(methylcarbamoyl)-2-phenylethyl)-3-(2-naphthyl)propionamide (332 mg, 0.82 mol) dissolved in methylene chloride (5 mL) and diisopropylethylamine (0.14 mL) were added and the mixture was stirred overnight under nitrogen atmosphere. The mixture was diluted with methylene chloride (50 mL), washed with water (50 mL), sodium hydrogen carbonate (30 mL, saturated), and sodium hydrogensulfate (30 mL, 5%). The phases were separated and the organic phase was dried with magnesium sulfate and evaporated in vacuo. The residue was chromatographed (silica, 2×40 cm) to afford 450 mg of ((3E)-1,1-dimethyl4-(N-methyl-N-((1R)-1-(N-methyl-N-((1R)-1-(methylcarbamoyl)-2-phenylethyl)carbamoyl)-2-(2-naphthyl)ethyl)carbamoyl)but-3-enyl)-carbamic acid tert-butyl ester.

Step J ((3E)-1,1-Dimethyl4-(methyl-((1R)-1-(methyl-((1R)-1-(methylcarbamoyl)-2-phenylethyl)carbamoyl)-2-(2-naphthyl)ethyl)carbamoyl)but-3-enyl)carbamic acid tert-butyl ester (403 mg, 0.63 mmol) was stirred in a mixture of trifluoroacetic acid (4 mL) and methylene chloride (4 mL) for 10 min. The volatiles were removed in vacuo and the crude product was chromatographed on silica (400 g) using a mixture of methylene chloride, ethanol and ammonia (25% in water) (80/18/2) as eluent. The isolated product was dissolved in 3M hydrochloric acid in ethyl acetate and evaporated, then redissolved in methylene chloride and evaporated twice to afford 140 mg of the title compound.

We claim:

1. A method for preparing a compound of formula I

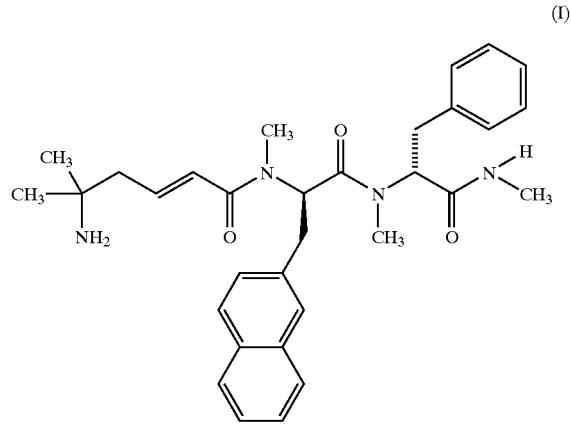

(I)

or a salt thereof, comprising (a) treating a compound of formula II

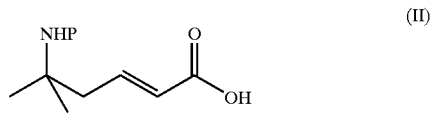

(II)

or a salt thereof, wherein P is a protecting group, with an agent that forms an amide or ester or mixed carbonic anhydride or anhydride or acid halide, in a solvent selected from the group consisting of an organic solvent, a mixture of organic solvents, and a mixture of organic solvent(s) and water, to form a compound of formula III;

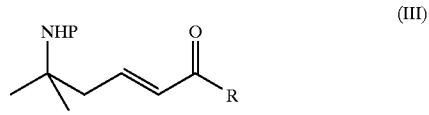

(III)

(b) removing (i) any excess agent that forms the ester or mixed anhydride, (ii) any excess of the compound of formula II, and (iii) the solvent used in the reaction of step (a);

(c) isolating the compound of formula III;
(d) reacting, for a period of time and under conditions effective to produce a compound of formula V, the isolated compound of formula III, or a salt thereof, wherein R together with the carbonyl moiety is an amide or ester or mixed carbonic anhydride or anhydride or acid halide, with a compound of formula (IV)

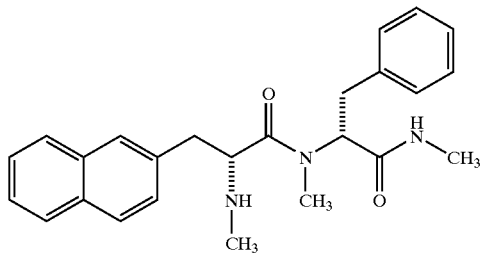

(IV)

in a solvent selected from an organic solvent, a mixture of organic solvents, and a mixture of organic solvent(s) and water, to produce the compound of formula (V)

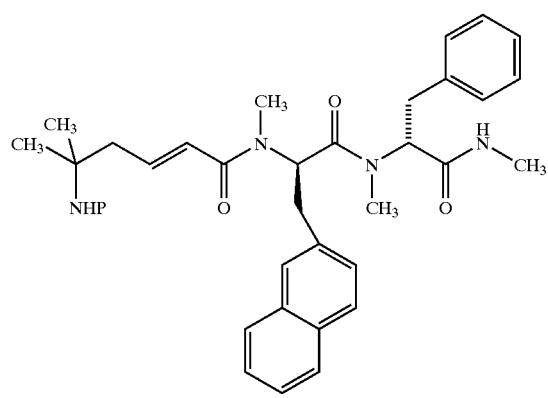

(V)

or a salt thereof,
(e) deprotecting the compound of formula V in a conventional manner to obtain the compound of formula (I);
(f) optionally converting the compound of formula (I) into a salt thereof; and
(g) isolating the compound of formula (I) or a salt thereof.

2. The method according to claim 1, wherein P is a group of formula —C(=O)—O—$C_{1-12}$alkyl or —C(=O)—O—$C_{1-12}$alkenyl, optionally substituted with one or more substituents selected from the group consisting of halogen, $C_{1-6}$alkyl, hetaryl, aryl and a fused-ring aromatic system.

3. The method according to claim 2, wherein P is selected from the group consisting of trichloroethyloxycarbonyl (Troc), tert-butoxycarbonyl (Boc), and N-fluorenylmethyloxycarbonyl (Fmoc).

4. The method according to claim 1, wherein said agent with which said compound of formula II is treated is selected from the group consisting of benzotriazole, isobutyl chloroformate, 3,4-dihydro-3-hydroxy-4-oxo-1,2,3-benzotriazine (DHOBt), N-hydroxy-benzotriazole (HOBt), N-hydroxy-succinimide (HOSu), and 1-hydroxy-7-azabenzotriazole (HOAt).

5. The method according to claim 4, wherein said agent is 3,4-dihydro-3-hydroxy-4-oxo-1,2,3-benzotriazine (DHOBt).

6. The method according to claim 1, wherein said solvent in step (b) is a mixture of an organic solvent and water.

7. A compound of formula (V)

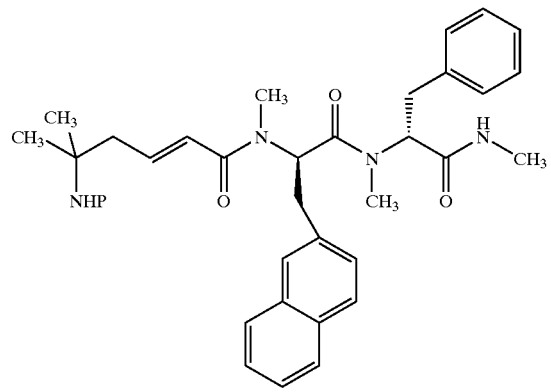

(V)

or a salt thereof, wherein P is selected from the group consisting of trichloroethyloxycarbonyl (Troc) and N-fluorenylmethyloxycarbonyl (Fmoc).

8. An isolated compound of formula III

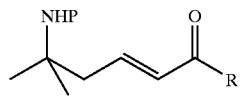

(III), wherein R together with the carbonyl moiety is an acid halide, and P is a protecting group.

9. The compound according to claim 8, wherein P is selected from the group consisting of trichloroethyloxycarbonyl (Troc), butoxycarbonyl (Boc), and N-fluorenylmethyloxycarbonyl (Fmoc).

10. An isolated compound of formula III

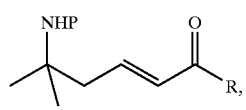

(III)

wherein R together with the carbonyl moiety is an ester, and P is a group of formula —C(=O)—O—R', optionally substituted with one or more substituents selected from the group consisting of halogen, hetaryl, aryl and a fused-ring aromatic system, wherein R' is selected from the group consisting of methyl, ethyl, propyl, n-butyl, pentyl, hexyl, isopropyl, sec-butyl, isopentyl, isohexyl, cyclopropyl, cyclobutyl, cyclopentyl and cyclohexyl.

11. The compound of claim 10, wherein P is selected from the group consisting of trichloroethyloxycarbonyl (Troc) and N-fluorenylmethyloxycarbonyl (Fmoc).

12. An isolated compound of formula III

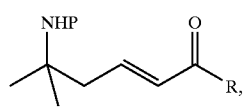

(III)

wherein R together with the carbonyl moiety is an ester, and P is a group of formula —C(=O)—O—$C_{1-12}$alkenyl, optionally substituted with one or more substituents selected from the group consisting of halogen, $C_{1-6}$alkyl, hetaryl, aryl and a fused-ring aromatic system.

13. An isolated compound of formula III

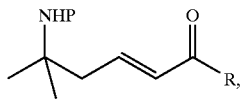

(III)

wherein R together with the carbonyl moiety is an ester obtained by reacting an agent selected from the group consisting of 3,4-dihydro-3-hydroxy-4-oxo-1,2,3-benzotriazine (DHOBt), N-hydroxy-benzotriazole (HOBt), N-hydroxy-succinimide (HOSu) and 1-(DHOBt), N-hydroxy-benzotriazole (HOBt), N-hydroxy-succinimide (HOSu) and 1-hydroxy-7-azabenzotriazole (HOAt) with the carboxylic acid moiety present in a compound of formula (II)

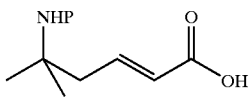

(II)

or a salt thereof, wherein P is a protecting group of formula —C(=O)—O—$C_{1-12}$alkenyl or —C(=O)—O—R', wherein R' is selected from the group consisting of methyl, ethyl, propyl, butyl, pentyl, hexyl, isopropyl, sec-butyl, isopentyl, isohexyl, cyclopropyl, cyclobutyl, cyclopentyl and cyclohexyl, and wherein said protecting group is optionally substituted with one or more substituents selected from the group consisting of halogen, $C_{1-6}$alkyl, hetaryl, aryl and a fused-ring aromatic system.

14. The compound according to claim 13, wherein said ester is obtained by reacting 3,4-dihydro-3-hydroxy-4-oxo-1,2,3-benzotriazine (DHOBt) with said carboxylic acid moiety present in said compound of formula II or salt thereof.

15. The compound according to claim 13, wherein P is trichloroethyloxycarbonyl (Troc) and said ester is obtained by reacting 3,4-dihydro-3-hydroxy-4-oxo-1,2,3-benzotriazine (DHOBt) with said carboxylic acid moiety present in said compound of formula II or a salt thereof.

16. An isolated compound of formula III

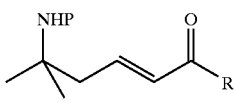

(III), wherein R together with the carbonyl moiety is an ester, and P is a group of formula C(=O)—O—R', optionally substituted with one or more substituents selected from the group consisting of halogen, $C_{1-6}$alkyl, hetaryl, aryl and a fused-ring aromatic system, wherein R' is selected from the group consisting of propyl, n-butyl, pentyl, hexyl, isopropyl, sec-butyl, isopentyl, isohexyl, cyclopropyl, cyclobutyl, cyclopentyl and cyclohexyl.

* * * * *

UNITED STATES PATENT AND TRADEMARK OFFICE
CERTIFICATE OF CORRECTION

| | | |
|---|---|---|
| PATENT NO. | : 6,784,158 B1 | Page 1 of 1 |
| APPLICATION NO. | : 09/325677 | |
| DATED | : August 31, 2004 | |
| INVENTOR(S) | : Jessen | |

It is certified that error appears in the above-identified patent and that said Letters Patent is hereby corrected as shown below:

Column 22, line 27, claim 16:
"propyl" should read --n-propyl--.
Column 22, line 27, claim 16:
delete "isopropyl".

Signed and Sealed this

Fourth Day of September, 2007

JON W. DUDAS
*Director of the United States Patent and Trademark Office*